(12) United States Patent
Moos et al.

(10) Patent No.: US 8,357,104 B2
(45) Date of Patent: Jan. 22, 2013

(54) ACTIVE STYLET SAFETY SHIELD

(75) Inventors: Kimberly A. Moos, Florissant, MO (US); David Rork Swisher, St. Charles, MO (US)

(73) Assignee: Coviden LP, Mansfield, MA (US)

( * ) Notice: Subject to any disclaimer, the term of this patent is extended or adjusted under 35 U.S.C. 154(b) by 962 days.

(21) Appl. No.: 11/933,864

(22) Filed: Nov. 1, 2007

(65) Prior Publication Data

US 2009/0118639 A1  May 7, 2009

(51) Int. Cl.
*A61B 5/00* (2006.01)
*A61B 10/00* (2006.01)
(52) U.S. Cl. .................................. 600/573; 600/562
(58) Field of Classification Search ............... 600/573, 600/575–584, 562–567; 128/919
See application file for complete search history.

(56) References Cited

U.S. PATENT DOCUMENTS

| | | | |
|---|---|---|---|
| 1,115,561 A | 11/1914 | Northey |
| 1,436,707 A | 11/1922 | Gaschke |
| 1,518,531 A | 12/1924 | Lung |
| 2,219,605 A | 10/1940 | Turkel |
| 2,854,976 A | 10/1958 | Heydrich |
| 3,254,533 A | 6/1966 | Tongret |
| 3,539,034 A | 11/1970 | Tafeen |
| 3,610,240 A | 10/1971 | Harautuneian |
| 3,681,991 A | 8/1972 | Eberly, Jr. |
| 3,729,998 A | 5/1973 | Mueller et al. |
| 3,822,598 A | 7/1974 | Hunter et al. |
| 3,884,230 A | 5/1975 | Wuff |
| 3,890,971 A | 6/1975 | Leeson et al. |
| 3,893,058 A | 7/1975 | Keith |
| 3,893,445 A | 7/1975 | Hofsess |
| 3,904,033 A | 9/1975 | Haerr |
| 3,915,003 A | 10/1975 | Adams |
| 3,946,613 A | 3/1976 | Silver |
| 3,976,070 A | 8/1976 | Dumont |
| 4,008,614 A | 2/1977 | Turner et al. |
| 4,010,737 A | 3/1977 | Vilaghy et al. |
| 4,026,287 A | 5/1977 | Haller |
| 4,099,518 A | 7/1978 | Baylis et al. |
| D249,475 S | 9/1978 | Turner et al. |
| 4,112,762 A | 9/1978 | Turner et al. |
| 4,139,009 A | 2/1979 | Alvarez |
| 4,142,517 A | 3/1979 | Stavropoulos et al. |
| 4,143,853 A | 3/1979 | Abramson |
| 4,160,450 A | 7/1979 | Doherty |
| 4,163,446 A | 8/1979 | Jamshidi |
| 4,177,797 A | 12/1979 | Baylis et al. |
| 4,183,248 A | 1/1980 | West |
| D255,997 S | 7/1980 | Maeda |
| 4,211,214 A | 7/1980 | Chikashige |

(Continued)

FOREIGN PATENT DOCUMENTS

DE    3805567 A1    8/1989

(Continued)

*Primary Examiner* — Brian Szmal
(74) *Attorney, Agent, or Firm* — Lisa E. Winsor, Esq.

(57) ABSTRACT

A bone needle assembly has a cannula and a stylet including a shaft received in a cannula shaft. A stylet safety shield is carried by the stylet to cover a sharp tip of the stylet shaft when removed from the cannula shaft after the bone is penetrated. The stylet includes a shield release device that moves the shield somewhat out of a handle member of the stylet when the stylet is released from the cannula, so that the safety shield can be more easily grasped.

16 Claims, 11 Drawing Sheets

U.S. PATENT DOCUMENTS

| | | |
|---|---|---|
| 4,256,119 A | 3/1981 | Gauthier |
| 4,258,713 A | 3/1981 | Wardlaw |
| 4,258,722 A | 3/1981 | Sessions et al. |
| 4,262,676 A | 4/1981 | Jamshidi |
| 4,266,543 A | 5/1981 | Blum |
| 4,266,555 A | 5/1981 | Jamshidi |
| 4,314,565 A | 2/1982 | Lee |
| 4,356,828 A | 11/1982 | Jamshidi |
| 4,392,859 A | 7/1983 | Dent |
| 4,403,617 A | 9/1983 | Tretinyak |
| 4,425,120 A | 1/1984 | Sampson et al. |
| 4,438,884 A | 3/1984 | O'Brien et al. |
| 4,469,109 A | 9/1984 | Mehl |
| 4,482,348 A | 11/1984 | Dent |
| 4,487,209 A | 12/1984 | Mehl |
| 4,513,754 A | 4/1985 | Lee |
| 4,543,966 A | 10/1985 | Islam et al. |
| 4,572,365 A | 2/1986 | Bruno et al. |
| 4,573,976 A | 3/1986 | Sampson et al. |
| 4,613,329 A | 9/1986 | Bodicky |
| 4,619,271 A | 10/1986 | Burger et al. |
| 4,630,616 A | 12/1986 | Tretinyak |
| 4,631,057 A | 12/1986 | Mitchell |
| 4,639,249 A | 1/1987 | Larson |
| 4,642,785 A | 2/1987 | Packard |
| 4,643,199 A | 2/1987 | Jennings, Jr. et al. |
| 4,643,200 A | 2/1987 | Jennings, Jr. et al. |
| 4,655,226 A | 4/1987 | Lee |
| 4,664,654 A | 5/1987 | Strauss |
| 4,676,783 A | 6/1987 | Jagger et al. |
| 4,681,567 A | 7/1987 | Masters et al. |
| 4,693,708 A | 9/1987 | Wanderer et al. |
| 4,695,274 A | 9/1987 | Fox |
| D292,493 S | 10/1987 | King |
| D292,494 S | 10/1987 | King |
| D293,215 S | 12/1987 | Bruno et al. |
| 4,723,943 A | 2/1988 | Spencer |
| 4,725,267 A | 2/1988 | Vaillancourt |
| 4,728,320 A | 3/1988 | Chen |
| 4,735,619 A | 4/1988 | Sperry et al. |
| 4,737,144 A | 4/1988 | Choksi |
| 4,738,663 A | 4/1988 | Bogan |
| 4,741,627 A | 5/1988 | Fukui |
| 4,743,233 A | 5/1988 | Schneider |
| 4,747,831 A | 5/1988 | Kulli |
| 4,747,836 A | 5/1988 | Luther |
| 4,747,837 A | 5/1988 | Hauck |
| 4,752,290 A | 6/1988 | Schramm |
| 4,762,516 A | 8/1988 | Luther et al. |
| 4,770,655 A | 9/1988 | Haber et al. |
| 4,772,272 A | 9/1988 | McFarland |
| 4,775,363 A | 10/1988 | Sandsdalen |
| 4,781,684 A | 11/1988 | Trenner |
| 4,781,692 A | 11/1988 | Jagger et al. |
| 4,785,826 A | 11/1988 | Ward |
| 4,790,329 A | 12/1988 | Simon |
| 4,790,827 A | 12/1988 | Haber et al. |
| 4,790,828 A | 12/1988 | Dombrowski et al. |
| 4,793,363 A | 12/1988 | Ausherman et al. |
| 4,795,432 A | 1/1989 | Karczmer |
| 4,804,371 A | 2/1989 | Vaillancourt |
| 4,804,372 A | 2/1989 | Laico et al. |
| 4,810,248 A | 3/1989 | Masters et al. |
| 4,813,426 A | 3/1989 | Haber et al. |
| 4,816,022 A | 3/1989 | Poncy |
| D300,728 S | 4/1989 | Ross |
| 4,819,659 A | 4/1989 | Sitar |
| 4,820,275 A | 4/1989 | Haber et al. |
| 4,826,488 A | 5/1989 | Nelson et al. |
| 4,826,490 A | 5/1989 | Byrne et al. |
| 4,826,491 A | 5/1989 | Schramm |
| 4,834,718 A | 5/1989 | McDonald |
| 4,838,280 A | 6/1989 | Haaga |
| 4,838,282 A | 6/1989 | Strasser et al. |
| 4,842,586 A | 6/1989 | Hogan |
| 4,846,809 A | 7/1989 | Sims |
| 4,900,307 A | 2/1990 | Kulli |
| 4,904,242 A | 2/1990 | Kulli |
| 4,906,235 A | 3/1990 | Roberts |
| 4,909,793 A | 3/1990 | Vining et al. |
| 4,911,694 A | 3/1990 | Dolan |
| 4,911,706 A | 3/1990 | Levitt |
| 4,915,702 A | 4/1990 | Haber |
| D307,558 S | 5/1990 | Messina et al. |
| 4,922,602 A | 5/1990 | Mehl |
| 4,927,414 A | 5/1990 | Kulli |
| 4,929,241 A | 5/1990 | Kulli |
| 4,931,044 A | 6/1990 | Beiter |
| 4,935,013 A | 6/1990 | Haber |
| 4,943,283 A | 7/1990 | Hogan |
| 4,944,725 A | 7/1990 | McDonald |
| 4,950,250 A | 8/1990 | Haber et al. |
| 4,952,207 A | 8/1990 | Lemieux |
| 4,955,866 A | 9/1990 | Corey |
| 4,958,625 A | 9/1990 | Bates et al. |
| 4,960,412 A | 10/1990 | Fink |
| 4,964,854 A | 10/1990 | Luther |
| 4,966,587 A | 10/1990 | Baumgart |
| 4,969,554 A | 11/1990 | Sawaya |
| 4,978,344 A | 12/1990 | Dombrowski et al. |
| 4,986,279 A | 1/1991 | O'Neill |
| 4,994,041 A | 2/1991 | Dombrowski et al. |
| 5,005,585 A | 4/1991 | Mazza |
| 5,012,818 A | 5/1991 | Joishy |
| 5,013,304 A | 5/1991 | Russell et al. |
| 5,031,634 A | 7/1991 | Simon |
| 5,036,860 A | 8/1991 | Leigh et al. |
| 5,047,044 A | 9/1991 | Smith et al. |
| 5,049,136 A | 9/1991 | Johnson |
| 5,051,109 A | 9/1991 | Simon |
| 5,053,017 A | 10/1991 | Chamuel |
| 5,057,085 A | 10/1991 | Kopans |
| 5,059,180 A | 10/1991 | McLees |
| 5,085,648 A | 2/1992 | Purdy et al. |
| 5,092,851 A | 3/1992 | Ragner |
| 5,102,394 A | 4/1992 | Lasaitis et al. |
| 5,108,374 A | 4/1992 | Lemieux |
| 5,109,849 A * | 5/1992 | Goodman et al. ............ 600/483 |
| 5,126,090 A | 6/1992 | Egolf et al. |
| 5,127,916 A | 7/1992 | Spencer et al. |
| 5,133,727 A | 7/1992 | Bales et al. |
| 5,135,504 A | 8/1992 | McLees |
| 5,147,327 A | 9/1992 | Johnson |
| 5,154,703 A | 10/1992 | Bonaldo |
| 5,171,229 A | 12/1992 | McNeil et al. |
| 5,172,702 A | 12/1992 | Leigh et al. |
| 5,176,256 A | 1/1993 | Sawaya |
| 5,183,468 A | 2/1993 | McLees |
| 5,195,533 A | 3/1993 | Chin et al. |
| 5,195,985 A | 3/1993 | Hall |
| 5,213,115 A | 5/1993 | Zytkovicz et al. |
| 5,215,525 A | 6/1993 | Sturman |
| 5,215,528 A | 6/1993 | Purdy et al. |
| 5,215,533 A | 6/1993 | Robb |
| 5,217,438 A | 6/1993 | Davis et al. |
| 5,228,451 A | 7/1993 | Bales et al. |
| 5,257,632 A | 11/1993 | Turkel et al. |
| 5,279,306 A | 1/1994 | Mehl |
| 5,279,563 A | 1/1994 | Brucker et al. |
| 5,279,591 A | 1/1994 | Simon |
| 5,282,477 A | 2/1994 | Bauer |
| 5,295,977 A | 3/1994 | Cohen et al. |
| 5,304,136 A | 4/1994 | Erskine et al. |
| 5,312,359 A | 5/1994 | Wallace |
| 5,314,406 A | 5/1994 | Arias et al. |
| 5,316,013 A | 5/1994 | Striebel, II et al. |
| 5,320,635 A | 6/1994 | Smith |
| 5,322,517 A | 6/1994 | Sircom et al. |
| 5,324,288 A | 6/1994 | Billings et al. |
| 5,328,482 A | 7/1994 | Sircom et al. |
| 5,331,971 A | 7/1994 | Bales et al. |
| 5,331,972 A | 7/1994 | Wadhwani et al. |
| 5,334,158 A | 8/1994 | McLees |
| 5,338,311 A | 8/1994 | Mahurkar |
| 5,338,314 A | 8/1994 | Ryan |
| 5,341,816 A | 8/1994 | Allen |
| 5,344,408 A | 9/1994 | Partika |

| | | | | | |
|---|---|---|---|---|---|
| 5,348,022 A | 9/1994 | Leigh et al. | 5,601,599 A | 2/1997 | Nunez |
| 5,348,544 A | 9/1994 | Sweeney et al. | 5,611,781 A | 3/1997 | Sircom et al. |
| 5,356,421 A | 10/1994 | Castro | 5,615,690 A | 4/1997 | Giurtino et al. |
| 5,357,974 A | 10/1994 | Baldridge | 5,616,135 A | 4/1997 | Thorne et al. |
| 5,368,045 A | 11/1994 | Clement et al. | 5,623,969 A | 4/1997 | Raines |
| 5,368,046 A | 11/1994 | Scarfone et al. | 5,624,459 A | 4/1997 | Kortenbach et al. |
| 5,370,623 A | 12/1994 | Kreamer | 5,630,506 A | 5/1997 | Thorne et al. |
| D354,921 S | 1/1995 | Narayanan | 5,630,837 A | 5/1997 | Crowley |
| 5,385,151 A | 1/1995 | Scarfone et al. | 5,632,555 A | 5/1997 | Gregory |
| 5,385,570 A | 1/1995 | Chin et al. | 5,634,473 A | 6/1997 | Goldenberg et al. |
| 5,389,104 A | 2/1995 | Hahnen et al. | 5,643,307 A | 7/1997 | Turkel et al. |
| 5,389,106 A | 2/1995 | Tower | 5,656,031 A | 8/1997 | Thorne et al. |
| 5,394,885 A | 3/1995 | Francese | 5,662,610 A | 9/1997 | Sircom |
| 5,395,375 A | 3/1995 | Turkel et al. | 5,666,965 A | 9/1997 | Bales et al. |
| 5,396,900 A | 3/1995 | Slater et al. | 5,669,883 A | 9/1997 | Scarfone et al. |
| 5,399,167 A | 3/1995 | Deniega | 5,672,161 A | 9/1997 | Allen et al. |
| 5,403,283 A | 4/1995 | Luther | 5,679,907 A | 10/1997 | Ruck |
| 5,405,323 A | 4/1995 | Rogers et al. | 5,685,852 A | 11/1997 | Turkel et al. |
| 5,405,388 A | 4/1995 | Fox | 5,685,862 A | 11/1997 | Mahurkar |
| 5,409,461 A | 4/1995 | Steinman | 5,687,907 A | 11/1997 | Holden |
| 5,411,486 A | 5/1995 | Zadini et al. | 5,690,619 A | 11/1997 | Erskine |
| 5,415,182 A | 5/1995 | Chin et al. | 5,693,022 A | 12/1997 | Haynes |
| 5,417,659 A | 5/1995 | Gaba | 5,693,031 A | 12/1997 | Ryan et al. |
| 5,417,709 A | 5/1995 | Slater et al. | 5,695,467 A | 12/1997 | Miyata et al. |
| 5,419,766 A | 5/1995 | Chang et al. | 5,695,521 A | 12/1997 | Anderhub |
| 5,421,522 A | 6/1995 | Bowen | 5,697,904 A | 12/1997 | Raines et al. |
| 5,423,766 A | 6/1995 | Di Cesare | 5,697,907 A | 12/1997 | Gaba |
| 5,425,718 A | 6/1995 | Tay et al. | 5,700,249 A | 12/1997 | Jenkins |
| 5,425,884 A | 6/1995 | Botz | 5,700,250 A | 12/1997 | Erskine |
| 5,429,138 A | 7/1995 | Jamshidi | 5,702,080 A | 12/1997 | Whittier et al. |
| 5,429,616 A | 7/1995 | Schaffer | 5,702,369 A | 12/1997 | Mercereau |
| 5,454,378 A | 10/1995 | Palmer et al. | 5,706,824 A | 1/1998 | Whittier |
| 5,456,267 A | 10/1995 | Stark | 5,707,392 A | 1/1998 | Kortenbach |
| 5,458,658 A | 10/1995 | Sircom | 5,713,368 A | 2/1998 | Leigh |
| 5,462,062 A | 10/1995 | Rubinstein et al. | 5,713,888 A | 2/1998 | Neuenfeldt et al. |
| 5,466,223 A | 11/1995 | Bressler et al. | 5,715,832 A | 2/1998 | Koblish et al. |
| 5,471,992 A | 12/1995 | Banik et al. | 5,718,688 A | 2/1998 | Wozencroft |
| 5,473,629 A | 12/1995 | Muramoto | 5,722,422 A | 3/1998 | Palmer et al. |
| 5,476,099 A | 12/1995 | Robinson et al. | 5,730,150 A | 3/1998 | Peppel et al. |
| 5,476,102 A | 12/1995 | Como et al. | 5,730,724 A | 3/1998 | Plishka et al. |
| 5,478,313 A | 12/1995 | White | 5,735,827 A | 4/1998 | Adwers et al. |
| 5,480,385 A | 1/1996 | Thorne et al. | 5,738,660 A | 4/1998 | Luther |
| 5,482,054 A | 1/1996 | Slater et al. | 5,738,665 A | 4/1998 | Caizza et al. |
| 5,487,734 A | 1/1996 | Thorne et al. | 5,746,753 A | 5/1998 | Sullivan et al. |
| 5,492,532 A | 2/1996 | Ryan et al. | 5,752,923 A | 5/1998 | Terwilliger |
| 5,501,675 A | 3/1996 | Erskine | D395,609 S | 6/1998 | Knieriem et al. |
| 5,507,296 A | 4/1996 | Bales et al. | 5,758,655 A | 6/1998 | Como Rodriguez et al. |
| 5,507,297 A | 4/1996 | Slater et al. | 5,776,157 A | 7/1998 | Thorne et al. |
| 5,507,298 A | 4/1996 | Schramm et al. | 5,795,336 A | 8/1998 | Romano et al. |
| 5,514,100 A | 5/1996 | Mahurkar | 5,807,275 A | 9/1998 | Jamshidi |
| 5,514,152 A | 5/1996 | Smith | 5,807,277 A | 9/1998 | Swaim |
| 5,522,398 A | 6/1996 | Goldenberg et al. | 5,810,744 A | 9/1998 | Chu et al. |
| 5,526,821 A | 6/1996 | Jamshidi | 5,817,069 A | 10/1998 | Arnett |
| 5,533,516 A | 7/1996 | Sahatjian | 5,823,970 A | 10/1998 | Terwilliger |
| 5,533,974 A | 7/1996 | Gaba | 5,823,971 A | 10/1998 | Robinson et al. |
| 5,538,009 A | 7/1996 | Byrne et al. | 5,823,997 A | 10/1998 | Thorne |
| 5,542,927 A | 8/1996 | Thorne et al. | 5,824,002 A | 10/1998 | Gentelia et al. |
| 5,549,565 A | 8/1996 | Ryan et al. | D400,806 S | 11/1998 | Tillack |
| 5,549,708 A | 8/1996 | Thorne et al. | D400,808 S | 11/1998 | Schwan |
| 5,553,624 A | 9/1996 | Francese et al. | 5,836,917 A | 11/1998 | Thorne et al. |
| 5,558,651 A | 9/1996 | Crawford et al. | 5,836,921 A | 11/1998 | Mahurkar |
| 5,562,629 A | 10/1996 | Haughton et al. | 5,840,044 A | 11/1998 | Dassa et al. |
| 5,562,633 A | 10/1996 | Wozencroft | 5,843,001 A | 12/1998 | Goldenberg |
| 5,562,683 A | 10/1996 | Chan | 5,848,692 A | 12/1998 | Thorne et al. |
| 5,569,217 A | 10/1996 | Luther | 5,853,393 A | 12/1998 | Bogert |
| 5,569,299 A | 10/1996 | Dill et al. | 5,860,955 A | 1/1999 | Wright et al. |
| 5,570,783 A | 11/1996 | Thorne et al. | 5,865,806 A | 2/1999 | Howell |
| 5,573,008 A | 11/1996 | Robinson et al. | 5,871,453 A | 2/1999 | Banik et al. |
| 5,573,510 A | 11/1996 | Isaacson | 5,873,886 A | 2/1999 | Larsen et al. |
| 5,578,015 A | 11/1996 | Robb | 5,879,332 A | 3/1999 | Schwemberger et al. |
| 5,584,809 A | 12/1996 | Gaba | 5,879,337 A | 3/1999 | Kuracina et al. |
| 5,584,810 A | 12/1996 | Brimhall | 5,879,338 A | 3/1999 | Mahurkar |
| 5,584,818 A | 12/1996 | Morrison | 5,882,337 A | 3/1999 | Bogert et al. |
| 5,586,990 A | 12/1996 | Hahnen et al. | 5,885,226 A | 3/1999 | Rubinstein et al. |
| 5,591,202 A | 1/1997 | Slater et al. | 5,891,105 A | 4/1999 | Mahurkar |
| 5,595,186 A | 1/1997 | Rubinstein et al. | 5,893,845 A | 4/1999 | Newby et al. |
| 5,599,310 A | 2/1997 | Bogert | 5,893,876 A | 4/1999 | Turkel et al. |
| 5,601,536 A | 2/1997 | Crawford et al. | 5,895,361 A | 4/1999 | Turturro |
| 5,601,585 A | 2/1997 | Banik et al. | 5,897,507 A | 4/1999 | Kortenbach et al. |

| Patent | Kind | Date | Inventor |
|---|---|---|---|
| 5,906,594 | A | 5/1999 | Scarfone et al. |
| 5,910,130 | A | 6/1999 | Caizza et al. |
| 5,910,132 | A | 6/1999 | Schultz |
| 5,911,705 | A | 6/1999 | Howell |
| 5,913,859 | A | 6/1999 | Shapira |
| 5,916,175 | A | 6/1999 | Bauer |
| 5,928,162 | A | 7/1999 | Giurtino et al. |
| 5,928,163 | A | 7/1999 | Roberts et al. |
| 5,928,200 | A | 7/1999 | Thorne et al. |
| 5,935,109 | A | 8/1999 | Donnan |
| 5,947,930 | A | 9/1999 | Schwemberger et al. |
| 5,951,489 | A | 9/1999 | Bauer |
| 5,951,525 | A | 9/1999 | Thorne et al. |
| 5,951,582 | A | 9/1999 | Thorne et al. |
| 5,954,696 | A | 9/1999 | Ryan |
| 5,954,698 | A | 9/1999 | Pike |
| 5,957,863 | A | 9/1999 | Koblish et al. |
| 5,957,887 | A | 9/1999 | Osterlind et al. |
| 5,957,892 | A | 9/1999 | Thorne |
| 5,961,526 | A | 10/1999 | Chu et al. |
| 5,961,534 | A | 10/1999 | Banik et al. |
| 5,964,717 | A | 10/1999 | Gottlieb et al. |
| 5,967,490 | A | 10/1999 | Pike |
| 5,976,115 | A | 11/1999 | Parris et al. |
| 5,979,840 | A | 11/1999 | Hollister et al. |
| 5,980,488 | A | 11/1999 | Thorne |
| 5,989,196 | A | 11/1999 | Chu et al. |
| 5,989,229 | A | 11/1999 | Chiappetta |
| 5,989,241 | A | 11/1999 | Plishka et al. |
| 5,993,426 | A | 11/1999 | Hollister |
| 6,000,846 | A | 12/1999 | Gregory et al. |
| 6,001,080 | A | 12/1999 | Kuracina et al. |
| 6,004,294 | A | 12/1999 | Brimhall et al. |
| 6,007,560 | A | 12/1999 | Gottlieb et al. |
| 6,015,391 | A | 1/2000 | Rishton et al. |
| 6,022,324 | A | 2/2000 | Skinner |
| 6,024,708 | A | 2/2000 | Bales et al. |
| 6,024,727 | A | 2/2000 | Thorne et al. |
| 6,033,369 | A | 3/2000 | Goldenberg |
| 6,036,361 | A | 3/2000 | Gregory et al. |
| 6,036,675 | A | 3/2000 | Thorne et al. |
| 6,047,729 | A | 4/2000 | Hollister et al. |
| 6,050,954 | A | 4/2000 | Mittermeier |
| 6,050,976 | A | 4/2000 | Thorne et al. |
| 6,053,877 | A | 4/2000 | Banik et al. |
| 6,063,037 | A | 5/2000 | Mittermeier et al. |
| 6,063,040 | A | 5/2000 | Owen et al. |
| 6,071,284 | A | 6/2000 | Fox |
| 6,080,115 | A | 6/2000 | Rubinstein |
| 6,083,176 | A | 7/2000 | Terwilliger |
| 6,083,202 | A | 7/2000 | Smith |
| 6,086,563 | A | 7/2000 | Moulton et al. |
| 6,090,078 | A | 7/2000 | Erskine |
| 6,090,108 | A | 7/2000 | McBrayer et al. |
| 6,095,967 | A | 8/2000 | Black et al. |
| 6,096,005 | A | 8/2000 | Botich et al. |
| 6,102,920 | A | 8/2000 | Sullivan et al. |
| 6,106,484 | A | 8/2000 | Terwilliger |
| 6,110,128 | A | 8/2000 | Andelin et al. |
| 6,110,129 | A | 8/2000 | Terwilliger |
| 6,110,176 | A | 8/2000 | Shapira |
| RE36,885 | E | 9/2000 | Blecher et al. |
| 6,117,108 | A | 9/2000 | Woehr et al. |
| 6,117,112 | A | 9/2000 | Mahurkar |
| 6,117,115 | A | 9/2000 | Hill et al. |
| 6,132,401 | A | 10/2000 | Van Der Meyden et al. |
| 6,135,110 | A | 10/2000 | Roy |
| 6,142,956 | A | 11/2000 | Kortenbach et al. |
| 6,142,957 | A | 11/2000 | Diamond et al. |
| 6,149,629 | A | 11/2000 | Wilson et al. |
| 6,171,284 | B1 | 1/2001 | Kao |
| 6,174,292 | B1 | 1/2001 | Kortenbach et al. |
| 6,193,671 | B1 | 2/2001 | Turturro et al. |
| 6,197,007 | B1 | 3/2001 | Thorne et al. |
| 6,203,527 | B1 | 3/2001 | Zadini et al. |
| 6,210,373 | B1 | 4/2001 | Allmon |
| 6,217,556 | B1 | 4/2001 | Ellingson et al. |
| 6,221,029 | B1 | 4/2001 | Mathis et al. |
| 6,221,047 | B1 | 4/2001 | Greene et al. |
| 6,224,569 | B1 | 5/2001 | Brimhall |
| 6,224,576 | B1 | 5/2001 | Thorne et al. |
| 6,234,773 | B1 | 5/2001 | Hill et al. |
| 6,254,575 | B1 | 7/2001 | Thorne, Jr. et al. |
| 6,261,242 | B1 | 7/2001 | Roberts et al. |
| 6,264,617 | B1 | 7/2001 | Bales et al. |
| D446,135 | S | 8/2001 | Chen |
| 6,273,874 | B1 | 8/2001 | Parris |
| 6,280,399 | B1 | 8/2001 | Rossin et al. |
| 6,280,401 | B1 | 8/2001 | Mahurkar |
| 6,280,419 | B1 | 8/2001 | Vojtasek |
| 6,280,420 | B1 | 8/2001 | Ferguson et al. |
| D448,314 | S | 9/2001 | Chen |
| 6,283,925 | B1 | 9/2001 | Terwilliger |
| 6,287,278 | B1 | 9/2001 | Woehr et al. |
| 6,293,700 | B1 | 9/2001 | Lund et al. |
| 6,302,852 | B1 | 10/2001 | Fleming, III et al. |
| 6,309,376 | B1 | 10/2001 | Alesi |
| 6,312,394 | B1 | 11/2001 | Fleming, III et al. |
| 6,315,737 | B1 | 11/2001 | Skinner |
| 6,321,782 | B1 | 11/2001 | Hollister |
| 6,322,537 | B1 | 11/2001 | Chang |
| 6,328,701 | B1 | 12/2001 | Terwillinger |
| 6,328,713 | B1 | 12/2001 | Hollister |
| 6,334,857 | B1 | 1/2002 | Hollister et al. |
| 6,336,915 | B1 | 1/2002 | Scarfone et al. |
| 6,340,351 | B1 | 1/2002 | Goldenberg |
| 6,358,252 | B1 | 3/2002 | Shapira |
| 6,358,265 | B1 | 3/2002 | Thorne, Jr. et al. |
| 6,361,525 | B2 | 3/2002 | Capes et al. |
| 6,379,333 | B1 | 4/2002 | Brimhall et al. |
| 6,379,338 | B1 | 4/2002 | Garvin |
| 6,383,144 | B1 | 5/2002 | Mooney |
| 6,406,459 | B1 | 6/2002 | Allmon |
| 6,409,701 | B1 | 6/2002 | Cohn et al. |
| 6,416,484 | B1 | 7/2002 | Miller et al. |
| 6,423,034 | B2 | 7/2002 | Scarfone et al. |
| 6,439,768 | B1 | 8/2002 | Wu et al. |
| 6,443,910 | B1 | 9/2002 | Krueger et al. |
| 6,443,927 | B1 | 9/2002 | Cook |
| 6,443,929 | B1 | 9/2002 | Kuracina et al. |
| 6,478,751 | B1 | 11/2002 | Krueger et al. |
| 6,485,468 | B2 | 11/2002 | Vojtasek |
| 6,485,473 | B1 | 11/2002 | Lynn |
| 6,488,663 | B1 | 12/2002 | Steg |
| 6,500,129 | B1 | 12/2002 | Mahurkar |
| 6,501,384 | B2 | 12/2002 | Chapman |
| 6,517,516 | B1 | 2/2003 | Caizza |
| 6,519,569 | B1 | 2/2003 | White et al. |
| 6,520,938 | B1 | 2/2003 | Funderburk et al. |
| 6,537,255 | B1 | 3/2003 | Raines |
| 6,537,259 | B1 | 3/2003 | Niemann |
| 6,544,194 | B1 | 4/2003 | Kortenbach et al. |
| 6,551,328 | B2 | 4/2003 | Kortenbach |
| 6,554,778 | B1 | 4/2003 | Fleming, III |
| 6,575,919 | B1 | 6/2003 | Reiley et al. |
| 6,582,402 | B1 | 6/2003 | Erskine |
| 6,582,446 | B1 | 6/2003 | Marchosky |
| 6,585,704 | B2 | 7/2003 | Luther et al. |
| 6,592,556 | B1 | 7/2003 | Thorne |
| 6,595,954 | B1 | 7/2003 | Luther et al. |
| 6,595,955 | B2 | 7/2003 | Ferguson et al. |
| 6,613,018 | B2 | 9/2003 | Bagga et al. |
| 6,616,604 | B1 | 9/2003 | Bass et al. |
| 6,616,630 | B1 | 9/2003 | Woehr et al. |
| 6,623,458 | B2 | 9/2003 | Woehr et al. |
| 6,626,850 | B1 | 9/2003 | Chau et al. |
| D480,977 | S | 10/2003 | Wawro et al. |
| D481,321 | S | 10/2003 | Knieriem et al. |
| 6,629,959 | B2 | 10/2003 | Kuracina et al. |
| 6,634,789 | B2 | 10/2003 | Babkes |
| 6,635,033 | B1 | 10/2003 | Hill et al. |
| 6,638,254 | B2 | 10/2003 | Nakagami |
| 6,641,562 | B1 | 11/2003 | Peterson |
| 6,652,486 | B2 | 11/2003 | Bialecki et al. |
| 6,652,490 | B2 | 11/2003 | Howell |
| 6,663,592 | B2 | 12/2003 | Rhad et al. |
| 6,673,047 | B2 | 1/2004 | Crawford et al. |
| 6,673,060 | B1 | 1/2004 | Fleming, III |

| | | |
|---|---|---|
| 6,682,510 B2 | 1/2004 | Niermann |
| 6,689,102 B2 | 2/2004 | Greene |
| 6,692,471 B2 | 2/2004 | Boudreaux |
| 6,695,814 B2 | 2/2004 | Greene et al. |
| 6,698,921 B2 | 3/2004 | Siefert |
| 6,699,221 B2 | 3/2004 | Vaillancourt |
| 6,702,786 B2 | 3/2004 | Olovson |
| 6,719,732 B2 | 4/2004 | Courteix |
| 6,723,075 B2 | 4/2004 | Davey et al. |
| 6,727,805 B2 | 4/2004 | Hollister et al. |
| 6,730,043 B2 | 5/2004 | Krueger et al. |
| 6,731,216 B2 | 5/2004 | Ho et al. |
| 6,740,063 B2 | 5/2004 | Lynn |
| 6,749,576 B2 | 6/2004 | Bauer |
| 6,749,588 B1 | 6/2004 | Howell et al. |
| 6,749,595 B1 | 6/2004 | Murphy |
| 6,755,793 B2 | 6/2004 | Lamoureux et al. |
| 6,761,704 B2 | 7/2004 | Crawford |
| 6,761,706 B2 | 7/2004 | Vaillancourt |
| 6,764,567 B2 | 7/2004 | Sperko et al. |
| 6,767,336 B1 | 7/2004 | Kaplan |
| 6,770,050 B2 | 8/2004 | Epstein |
| 6,770,053 B2 | 8/2004 | Scarfone et al. |
| 6,796,962 B2 | 9/2004 | Ferguson et al. |
| 6,798,348 B1 | 9/2004 | Wilker et al. |
| 6,811,308 B2 | 11/2004 | Chapman |
| 6,821,267 B2 | 11/2004 | Veillon, Jr. et al. |
| 6,827,488 B2 | 12/2004 | Knieriem et al. |
| 6,832,990 B2 | 12/2004 | Kortenbach et al. |
| 6,832,992 B2 | 12/2004 | Wilkinson |
| 6,839,651 B2 | 1/2005 | Lantz et al. |
| 6,846,314 B2 | 1/2005 | Shapira |
| 6,849,051 B2 | 2/2005 | Sramek et al. |
| 6,855,128 B2 | 2/2005 | Swenson |
| 6,855,130 B2 | 2/2005 | Saulenas et al. |
| 6,860,871 B2 | 3/2005 | Kuracina et al. |
| 6,875,183 B2 | 4/2005 | Cervi |
| 6,890,308 B2 | 5/2005 | Islam |
| 6,902,546 B2 | 6/2005 | Ferguson |
| 6,916,292 B2 | 7/2005 | Morawski et al. |
| 6,916,311 B2 | 7/2005 | Vojtasek |
| 6,916,314 B2 | 7/2005 | Schneider |
| 6,923,813 B2 | 8/2005 | Phillips et al. |
| D512,506 S | 12/2005 | Layne et al. |
| D512,924 S | 12/2005 | Ikeda |
| 6,976,783 B2 | 12/2005 | Chen |
| 6,981,948 B2 | 1/2006 | Pellegrino et al. |
| 6,984,213 B2 | 1/2006 | Horner et al. |
| 6,984,216 B2 | 1/2006 | Sendijarevic et al. |
| 6,989,003 B2 | 1/2006 | Wing et al. |
| 7,004,927 B2 | 2/2006 | Ferguson et al. |
| 7,008,402 B2 | 3/2006 | Ferguson et al. |
| 7,018,343 B2 | 3/2006 | Plishka et al. |
| 7,021,824 B2 | 4/2006 | Wawro et al. |
| 7,033,324 B2 | 4/2006 | Giusti et al. |
| 7,036,984 B2 | 5/2006 | Penney et al. |
| 7,063,703 B2 | 6/2006 | Reo |
| 7,112,191 B2 | 9/2006 | Daga |
| 7,118,552 B2 | 10/2006 | Shaw et al. |
| 7,207,973 B2 | 4/2007 | Barrelle |
| 7,214,208 B2 | 5/2007 | Vaillancourt |
| 7,226,434 B2 | 6/2007 | Carlyon et al. |
| 7,238,169 B2 | 7/2007 | Takagi |
| 7,247,148 B2 | 7/2007 | Murashita |
| 7,255,475 B2 | 8/2007 | Quinn et al. |
| 7,316,507 B2 | 1/2008 | Sisk et al. |
| 2001/0004970 A1 | 6/2001 | Hollister et al. |
| 2001/0018573 A1 | 8/2001 | Woehr |
| 2001/0021827 A1 | 9/2001 | Ferguson et al. |
| 2001/0027298 A1 | 10/2001 | Vojtasek |
| 2001/0029356 A1 | 10/2001 | Vojtasek |
| 2001/0047154 A1 | 11/2001 | Jepson et al. |
| 2002/0004650 A1 | 1/2002 | Kuracina et al. |
| 2002/0021827 A1 | 2/2002 | Smith et al. |
| 2002/0151850 A1 | 10/2002 | Ferguson et al. |
| 2002/0169418 A1 | 11/2002 | Menzi et al. |
| 2002/0177812 A1 | 11/2002 | Moulton et al. |
| 2002/0193745 A1 | 12/2002 | Ferguson |
| 2003/0002562 A1 | 1/2003 | Yerlikaya et al. |
| 2003/0036731 A1 | 2/2003 | Wilkinson et al. |
| 2003/0060773 A1 | 3/2003 | Nguyen |
| 2003/0100868 A1 | 5/2003 | Ferguson et al. |
| 2003/0114797 A1 | 6/2003 | Vaillancourt et al. |
| 2003/0144627 A1 | 7/2003 | Woehr et al. |
| 2003/0176810 A1 | 9/2003 | Maahs et al. |
| 2003/0191438 A1 | 10/2003 | Ferguson et al. |
| 2003/0195471 A1 | 10/2003 | Woehr et al. |
| 2003/0220617 A1 | 11/2003 | Dickerson |
| 2004/0071182 A1 | 4/2004 | Quinn et al. |
| 2004/0077973 A1 | 4/2004 | Groenke et al. |
| 2004/0078002 A1 | 4/2004 | Rhad et al. |
| 2004/0078003 A1 | 4/2004 | Smith et al. |
| 2004/0078007 A1 | 4/2004 | Nguyen |
| 2004/0092889 A1 | 5/2004 | Ferguson et al. |
| 2004/0133167 A1 | 7/2004 | Ferguson et al. |
| 2004/0153005 A1 | 8/2004 | Krueger |
| 2004/0171989 A1 | 9/2004 | Horner et al. |
| 2004/0186434 A1 | 9/2004 | Harding et al. |
| 2004/0225260 A1 | 11/2004 | Villa et al. |
| 2004/0236288 A1 | 11/2004 | Howell et al. |
| 2004/0236289 A1 | 11/2004 | Ferguson et al. |
| 2005/0027263 A1 | 2/2005 | Woehr et al. |
| 2005/0043691 A1 | 2/2005 | Ferguson |
| 2005/0054987 A1 | 3/2005 | Perez et al. |
| 2005/0059937 A1 | 3/2005 | Ferguson |
| 2005/0070850 A1 | 3/2005 | Albrecht |
| 2005/0070851 A1 | 3/2005 | Thompson et al. |
| 2005/0070855 A1 | 3/2005 | Ferguson et al. |
| 2005/0075609 A1 | 4/2005 | Latona |
| 2005/0090763 A1 | 4/2005 | Wang |
| 2005/0090764 A1 | 4/2005 | Wang |
| 2005/0096592 A1 | 5/2005 | Carlyon et al. |
| 2005/0113716 A1 | 5/2005 | Mueller, Jr. et al. |
| 2005/0119652 A1 | 6/2005 | Vetter et al. |
| 2005/0131345 A1 | 6/2005 | Miller |
| 2005/0137500 A1 | 6/2005 | Wingler |
| 2005/0165404 A1 | 7/2005 | Miller |
| 2005/0182362 A1 | 8/2005 | Sircom et al. |
| 2005/0192536 A1 | 9/2005 | Takagi et al. |
| 2005/0203459 A1 | 9/2005 | Alchas |
| 2005/0267383 A1 | 12/2005 | Groenke et al. |
| 2005/0273057 A1 | 12/2005 | Popov |
| 2005/0277845 A1 | 12/2005 | Cooke et al. |
| 2005/0288605 A1 | 12/2005 | Pellegrino et al. |
| 2006/0036217 A1 | 2/2006 | Doyle |
| 2006/0052721 A1 | 3/2006 | Dunker et al. |
| 2006/0064101 A1 | 3/2006 | Arramon |
| 2006/0116603 A1 | 6/2006 | Shibazaki et al. |
| 2006/0173414 A1 | 8/2006 | Buetikofer et al. |
| 2006/0178625 A1 | 8/2006 | Lim et al. |
| 2006/0189934 A1 | 8/2006 | Kuracina et al. |
| 2006/0189936 A1 | 8/2006 | Carlyon et al. |
| 2006/0200195 A1 | 9/2006 | Yang |
| 2006/0276772 A1 | 12/2006 | Moos et al. |
| 2007/0110122 A1 | 5/2007 | Sisk et al. |
| 2007/0116089 A1 | 5/2007 | Bisch et al. |
| 2008/0112461 A1 | 5/2008 | Bisch et al. |
| 2008/0294065 A1 | 11/2008 | Waldhoff et al. |

FOREIGN PATENT DOCUMENTS

| | | |
|---|---|---|
| EP | 0750915 A2 | 1/1997 |
| EP | 1358846 A1 | 11/2003 |
| JP | 6-241914 A | 9/1994 |
| WO | 9622800 A1 | 8/1996 |
| WO | 9742989 A1 | 11/1997 |
| WO | 2004014464 A1 | 2/2004 |
| WO | 2004060138 | 7/2004 |
| WO | 2004091687 A2 | 10/2004 |
| WO | 2005009246 | 2/2005 |
| WO | 2005042073 A1 | 5/2005 |
| WO | 2005053774 A1 | 6/2005 |
| WO | 2005060679 | 7/2005 |

* cited by examiner

ACTIVE STYLET SAFETY SHIELD

BACKGROUND OF THE INVENTION

The present invention relates generally to a stylet safety shield.

Needle assemblies have particular, although not exclusive application in the field of medicine and have tubular needles with sharpened ends for use in piercing the skin to withdraw materials as needed. The needle is supported by some other structure that is used to manipulate the needle. The most common example is a syringe. However, some needle assemblies require the application of substantial force in use. One example of such a needle assembly is a bone marrow needle assembly that is used to penetrate cortical bone to reach the intramedullary canal for withdrawing liquid and/or a biopsy sample of bore marrow, or for infusing the canal with a selected material. Typically, the needle includes a cannula and a stylet that is received in the cannula and has a hard, sharp tip that can penetrate cortical bone. The tip projects out from the distal end of the cannula. The stylet can be withdrawn from the cannula after the needle penetrates the bone so that the hollow interior of the cannula can be used as a conduit for liquid or a receptacle to collect bone marrow.

In order to penetrate cortical bone, a substantial amount of force must be applied to the needle. For this reason, bone needle assemblies conventionally mount the needle in a handle that is sized and shaped so that the technician may comfortably grip the handle and apply the force necessary to penetrate the bone. The handle may comprise a stylet handle member 16 that mounts the stylet and a cannula handle member 18 that mounts the cannula. The two handle members are removably securable together to form the handle when the stylet is inserted into the cannula so that the stylet handle member 16 is in contact with the palm of the technician's hand in use, and the cannula handle member 18 receives the technician's fingers.

Some needle assemblies, including bone needle assemblies, have associated safety mechanisms that shield the sharp tips of the needle components when they are not needed and after they have become contaminated with potentially hazardous biological material. For example, one conventional type of bone needle assembly 10 includes a safety shield slidably received on the stylet for shielding the tip of the stylet. When the stylet is received in the cannula and the stylet handle member 16 is secured to the cannula handle member 18, the stylet safety shield is releasably secured within a cavity of the cannula handle member 18 and is housed within an enclosure defined by the cavity in the cannula handle member and a cavity in the stylet handle member. The stylet safety shield remains secured to the cannula handle member 18 when the stylet handle member 16 is removed from the cannula handle member and the stylet is withdrawn from the cannula. The stylet slides through the stylet safety shield as the stylet is withdrawn from the cannula until the mechanism in the safety shield fixedly engages the stylet at the stylet tip. As the technician continues to pull the stylet handle member 16 away from the cannula handle member 18 after the shield fixedly engages the stylet, the safety shield disengages the cannula handle member, and the stylet with the shield disposed over its tip is separated from the cannula.

Although the conventional stylet safety shield design described above is an easy, passive mechanism that ensures that the tip of the stylet will be covered after use and removal from the cannula, drawbacks have been realized and identified by the applicants. For instance, a desired bone marrow sample may not be retrieved on the first attempt, requiring reuse of the needle assembly. If the shield is automatically locked over the tip, it will be very difficult to expose the tip again for use. Moreover, in attempting to re-expose the tip, the danger of a stick is greatly magnified. Thus, the passive shield may lead to the very thing it was supposed to prevent.

SUMMARY OF THE INVENTION

In one aspect of the present invention a biopsy needle assembly generally comprises a cannula including a cannula handle and a cannula shaft extending outward from the handle. The cannula shaft has an axial passage extending through a proximal end of the shaft secured to the handle and a sharp distal tip of the shaft. A stylet includes a stylet handle and a stylet shaft extending outward from the stylet handle. The stylet shaft has a sharp distal tip and is adapted to be slidably received in the axial passage of the cannula shaft. The stylet handle is adapted to be releasably connected to the cannula handle when the stylet shaft is received in the cannula shaft to form a handle of the needle assembly. A safety shield includes a locking mechanism configurable between an unlocked configuration, in which the locking mechanism permits the shield to be moved axially along the stylet shaft when the shield is generally proximal of the tip of the stylet shaft, and a locked configuration, in which the locking mechanism substantially prevents axial movement of the shield when the shield is at a location covering the tip of the stylet shaft. The shield and the stylet are adapted for releasable interengagement when the stylet and cannula are connected to each other with a force greater than any force interengaging the shield and the cannula whereby the shield moves with the stylet after the stylet handle and the cannula handle are released from securement and as the stylet shaft is axially withdrawn from the cannula shaft. A shield release device mounted on the stylet is operable for pushing the safety shield in a direction out of the stylet handle.

In another aspect of the present invention, a method of using a biopsy needle assembly generally comprises penetrating the skin with a stylet needle and cannula needle of the biopsy needle assembly. A stylet handle mounting the stylet needle is disconnected from the cannula handle mounting the cannula needle. The stylet handle and needle are separated from the cannula handle and needle so that a stylet needle safety shield at least partially disposed in the stylet handle moves with the stylet handle. The safety shield is urged with a shield release device from a location interior of the stylet handle outward from the interior of the stylet handle.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DRAWINGS

Figure 1:
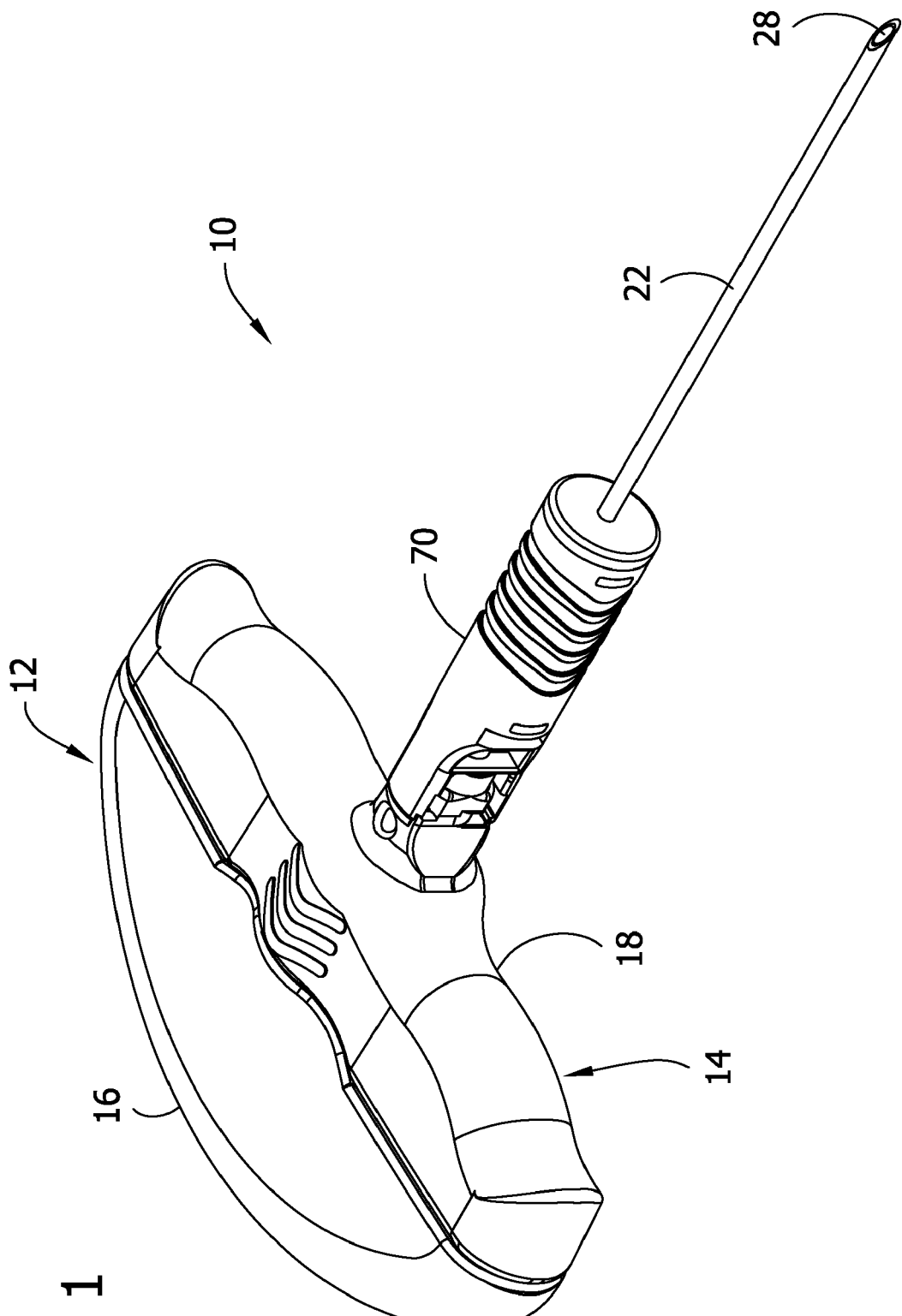
FIG. 1 is a perspective of a bone marrow needle assembly.

Referring now to the drawings and in particular to FIG. 1, a bone needle assembly is generally indicated at 10. The bone needle assembly includes a stylet 12 and a cannula 14 that may be releasably secured together to form the assembled bone needle assembly 10. The stylet 12 and the cannula 14 each include a handle member designated at 16 and 18, respectively, and a shaft (or "needle"), designated at 20 and 22, respectively. Each of the shafts 20, 22 is mounted on and extends outward from its corresponding handle member 16, 18. The cannula shaft 22 is generally cylindrical and defines an axial passage that is sized and shaped to removably receive the rod-shaped stylet shaft 20 so that the shafts together form a needle of the bone needle assembly 10 and the tips of the shafts together form a tip of the needle. The stylet handle member 16 is releasably securable to the cannula handle member 18 when the stylet shaft 20 is received in the cannula shaft 22 to form a handle of the bone needle assembly 10. The handle members 16, 18 are releasably securable by a bayonet connection that requires one of the stylet 12 and the cannula 14 to be rotated 90 degrees about a longitudinal axis to lock and unlock the handle members. Other ways of releasably securing the stylet 12 to the cannula 14 are within the scope of the invention. When the handle members are secured together, the stylet handle member 16 constitutes a proximal handle member because it is nearer to the technician during use, and the cannula handle member 18 constitutes a distal handle member because it is farther from the technician during use.

Figure 2:
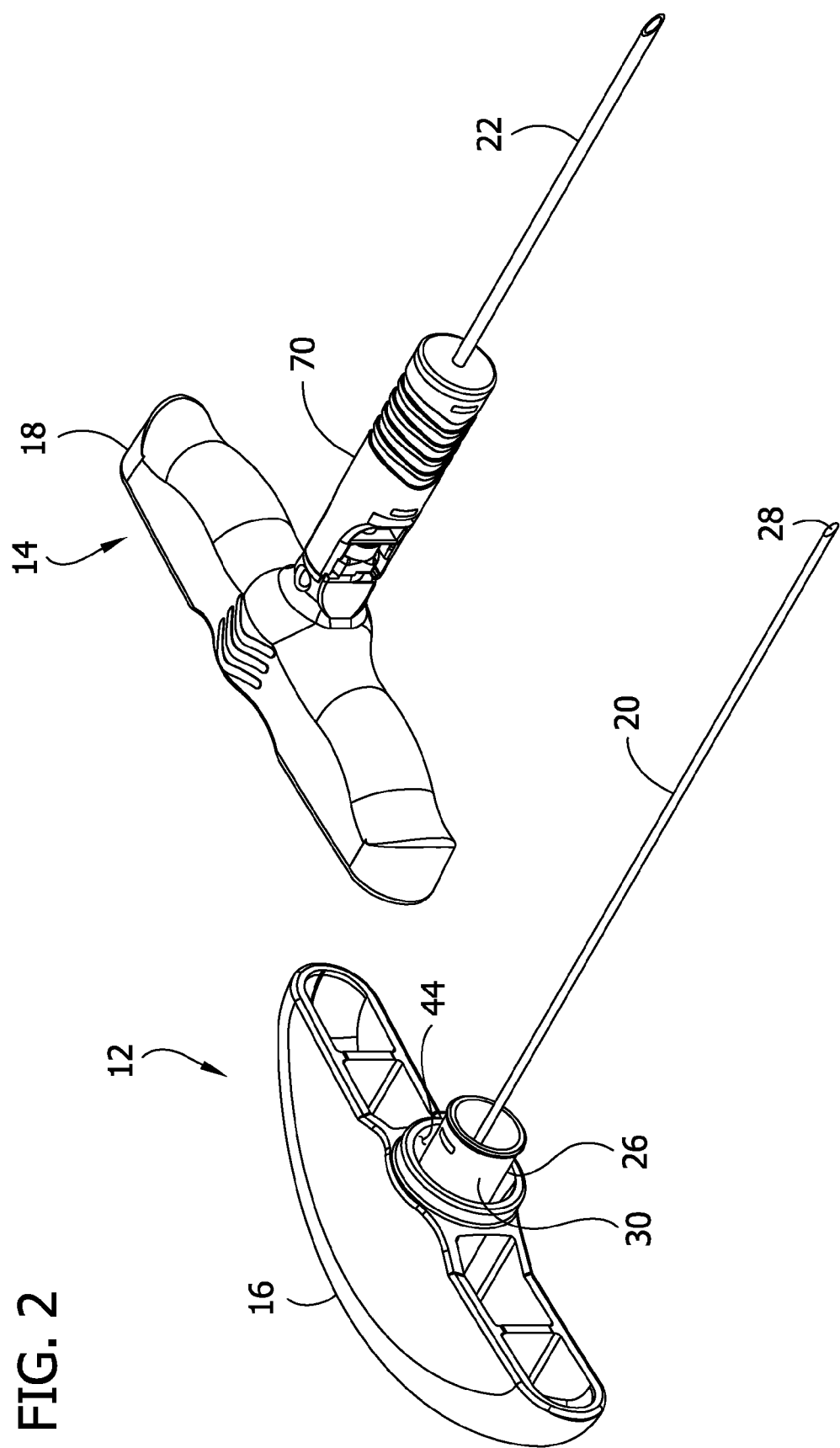
FIG. 2 is the perspective of FIG. 1, but with a stylet of the assembly separated from a cannula.
Figure 3:
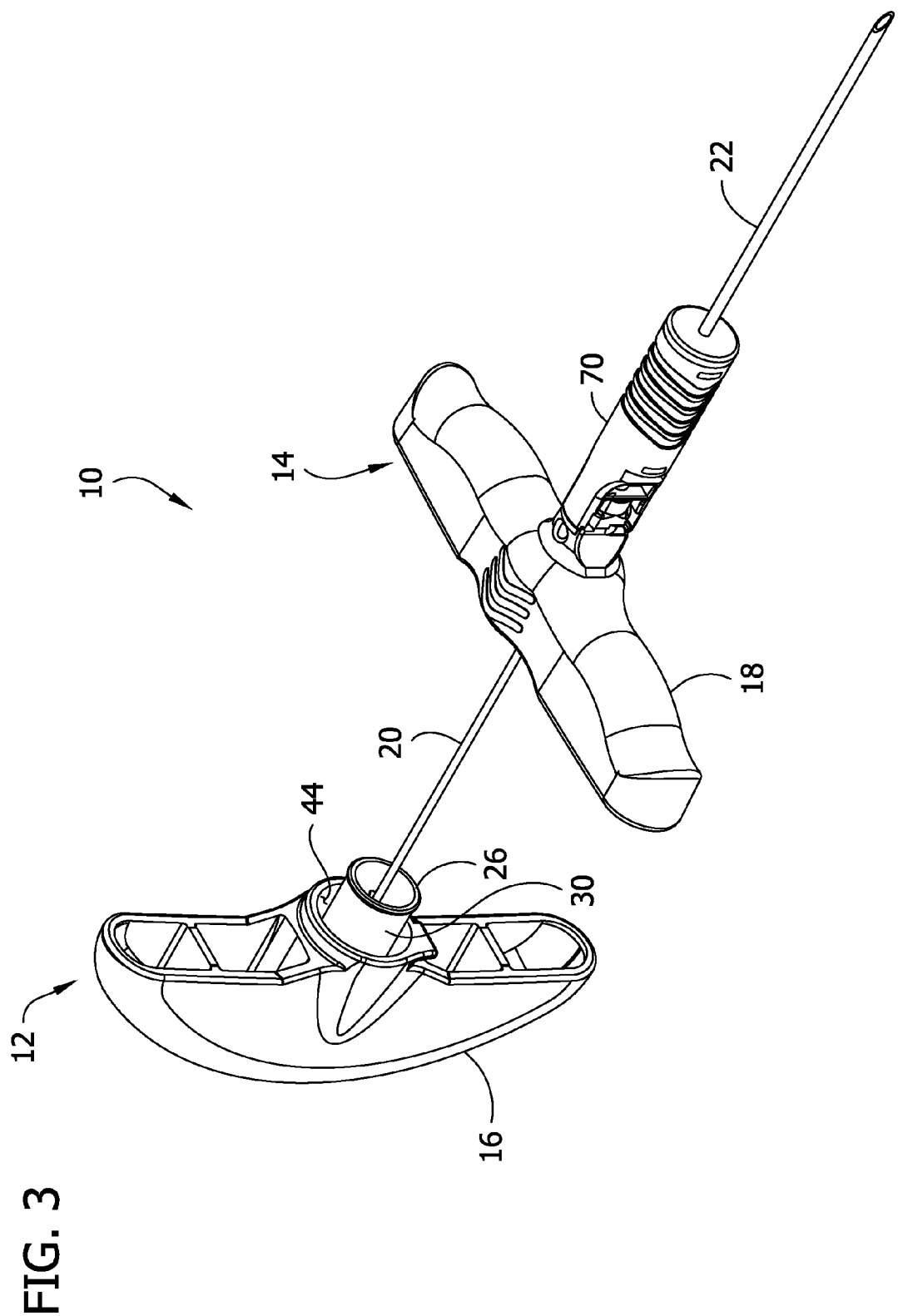
FIG. 3 is the perspective of FIG. 1, but with the stylet being separated from the cannula.
Figure 4:
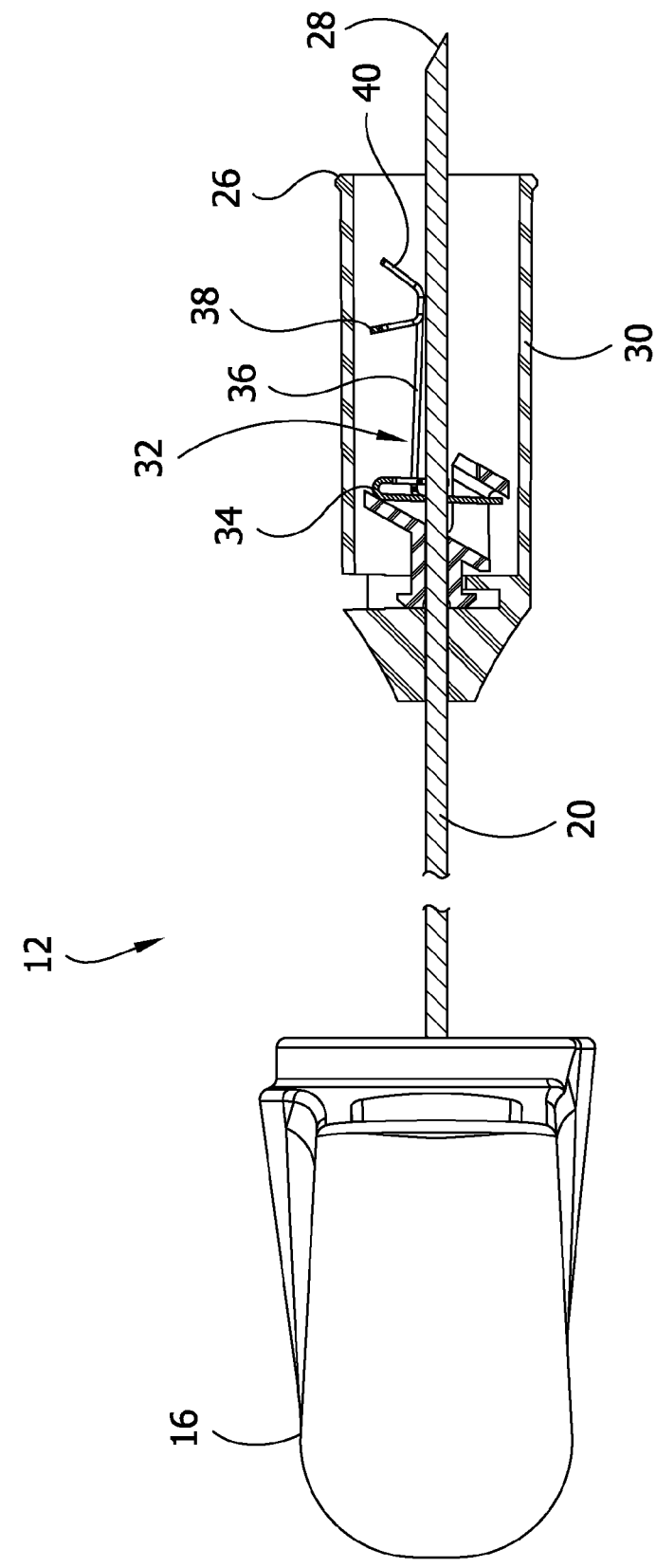
FIG. 4 is a partial fragmentary section of a needle and safety shield of the stylet showing a locking member not engaged.
Figure 5:
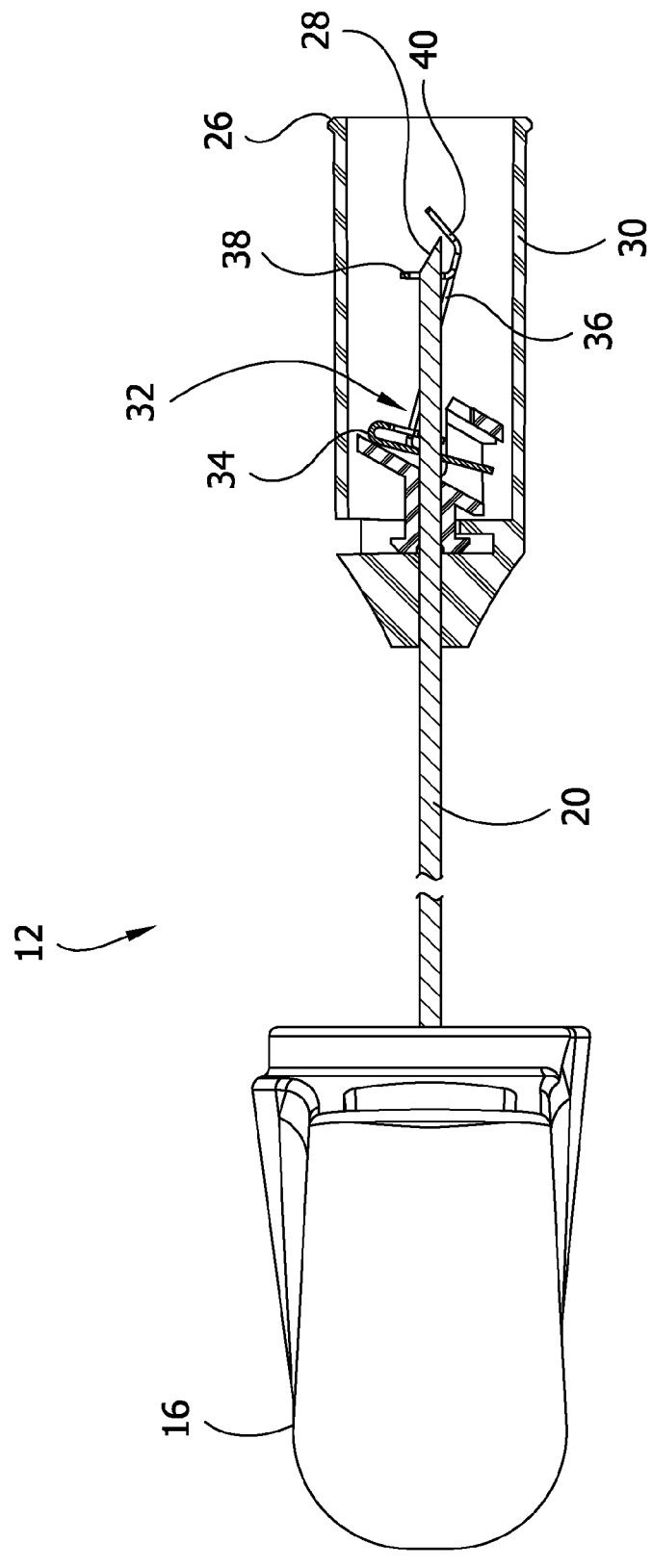
FIG. 5 is the section of FIG. 4, but showing the locking mechanism engaged with the needle.

The stylet 12 includes a safety shield 26 slidably received on the stylet shaft 20 for covering a sharp tip 28 of the shaft after the stylet is separated from the cannula 14 (FIG. 2). The safety shield 26 includes a generally tubular housing 30 and a locking mechanism (generally indicated at 32 supported within the housing. The locking mechanism 32 inside the safety shield 26 comprises a canting member including a base 34 having a hole and a pair of arms 36 (only one is shown) extending generally axially from the base (see, FIG. 4). The arms 36 are connected together by a U-shaped member 38 at their ends and each has an upwardly (as oriented in the figures) bent tab 40 (only one is shown) projecting axially outward from the end. Before the locking mechanism 32 is activated to lock the safety shield 26 in position, the ends of the arms 36 ride on the exterior surface of the cannula shaft 22. This holds the canting member so that the base 34 is generally orthogonal to the longitudinal axis of the stylet shaft 20. In that configuration, the base 38 can move along the stylet shaft 20 with the safety shield 26, and the cannula shaft 22 slides unimpeded through the hole in the base. Once the ends of the arms 36 pass the distal tip 28 of the stylet shaft 20, the locking mechanism 32 is spring biased so that the ends of the arms move in a generally radial direction toward an opposite side of the longitudinal axis of the stylet shaft 20. This causes the base 34 of the canting member to cant relative to the axis of the stylet shaft 20 so that the hole in the base is no longer orthogonal to the axis of the stylet shaft. As a result, the base 34 at the edge of the hole grippingly engages the stylet shaft 20 to lock the safety shield 26 in place. It will be understood that a locking mechanism could take on other forms than shown and described without departing from the scope of the present invention. Moreover, a canting member may take on other configurations (e.g., having only a single arm) within the scope of the present invention.

When bone needle assembly 10 is assembled (i.e., the stylet shaft 20 is received in the cannula shaft 22 and the handle members 16, 18 are secured together), the stylet shield 26 is in an initial position disposed adjacent a proximal end of the stylet shaft so that a distal portion of the shield is disposed in a receptacle (not shown) formed in the proximal end of the cannula handle member and a proximal portion of the shield is disposed in a cavity 44 in the stylet handle member 16. Thus, when the bone needle assembly 10 is assembled, the safety shield 26 is substantially concealed within the assembled handle.

The distal portion of the stylet safety shield 26 and the proximal end of the cannula handle member 18 are substantially free from connection with each other when the shield is received in the cannula handle member receptacle. The shield 26 and cannula handle member 18 can be said not to be interengaged, although they contact each other. As a result, after the bayonet connection of the stylet and cannula handle members 16, 18 is released, the cannula handle member will not retain the shield 26. The shield does have interengagement with the stylet handle member 16. First, the locking mechanism 32 frictionally engages the stylet shaft 20. Second, the sides of the shield 26 may wedge against walls 46 defining the cavity 44 in the stylet handle member 16 (see, FIG. 6). In the illustrated embodiments, both forms of engagement are present, but it will be understood that only one of these, or an entirely different form of interengagement may be employed within the scope of the present invention. The stylet shaft 20 will not slide through the safety shield 26, but instead the stylet shield will move conjointly with the stylet shaft as the stylet shaft is axially withdrawn from the cannula shaft 22.

The bone needle assembly 10 of the present invention does not have a passively activated safety shield (i.e., one which covers and locks onto the stylet tip automatically when the stylet is separated from the cannula). In the illustrated embodiment, the technician must actively supply the necessary pushing or pulling force to slide the shield 26 distally along the stylet shaft 20. It is understood that there may be some connection between the stylet shield 26 and the cannula handle member 18 when the needle assembly is assembled as long as the connection does not result in a counter force that is greater than the static force shield and the stylet 12.

Once the stylet 12 is separated from the cannula 14, it could be difficult for the technician to grasp the exposed distal end of the stylet shield 26 extending out from the stylet handle to move the shield along the stylet shaft 20 to the sharp tip 28. For example, perhaps only about one quarter of the length of the shield 26 may project from the stylet handle member 16 in the retracted position shown in FIG. 6. Further, the shield 26 may become lodged within the stylet handle member 16 and it may be difficult to dislodge the shield. Accordingly, in the illustrated embodiment, a shield release device, generally indicated at 50, is disposed in the cavity 44 of the stylet handle member 16 to urge the shield 26 distally along the stylet shaft 20 an axial distance D (see, FIG. 7) from its initial position (FIG. 6) within the handle member as the stylet 12 is being withdrawn from the cannula.

Figure 6:
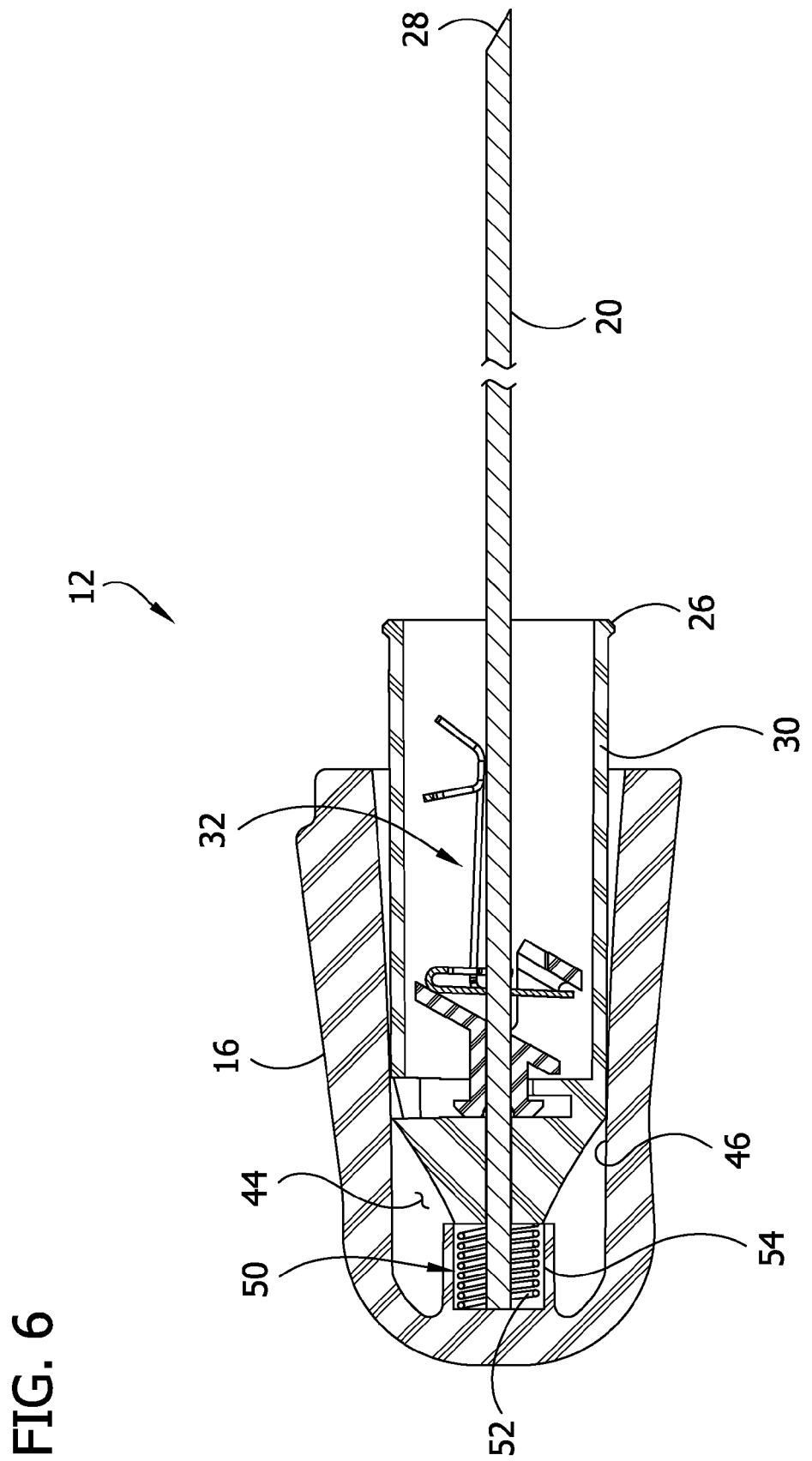
FIG. 6 is a fragmentary section of the stylet showing the safety shield in a retracted position.
Figure 7:
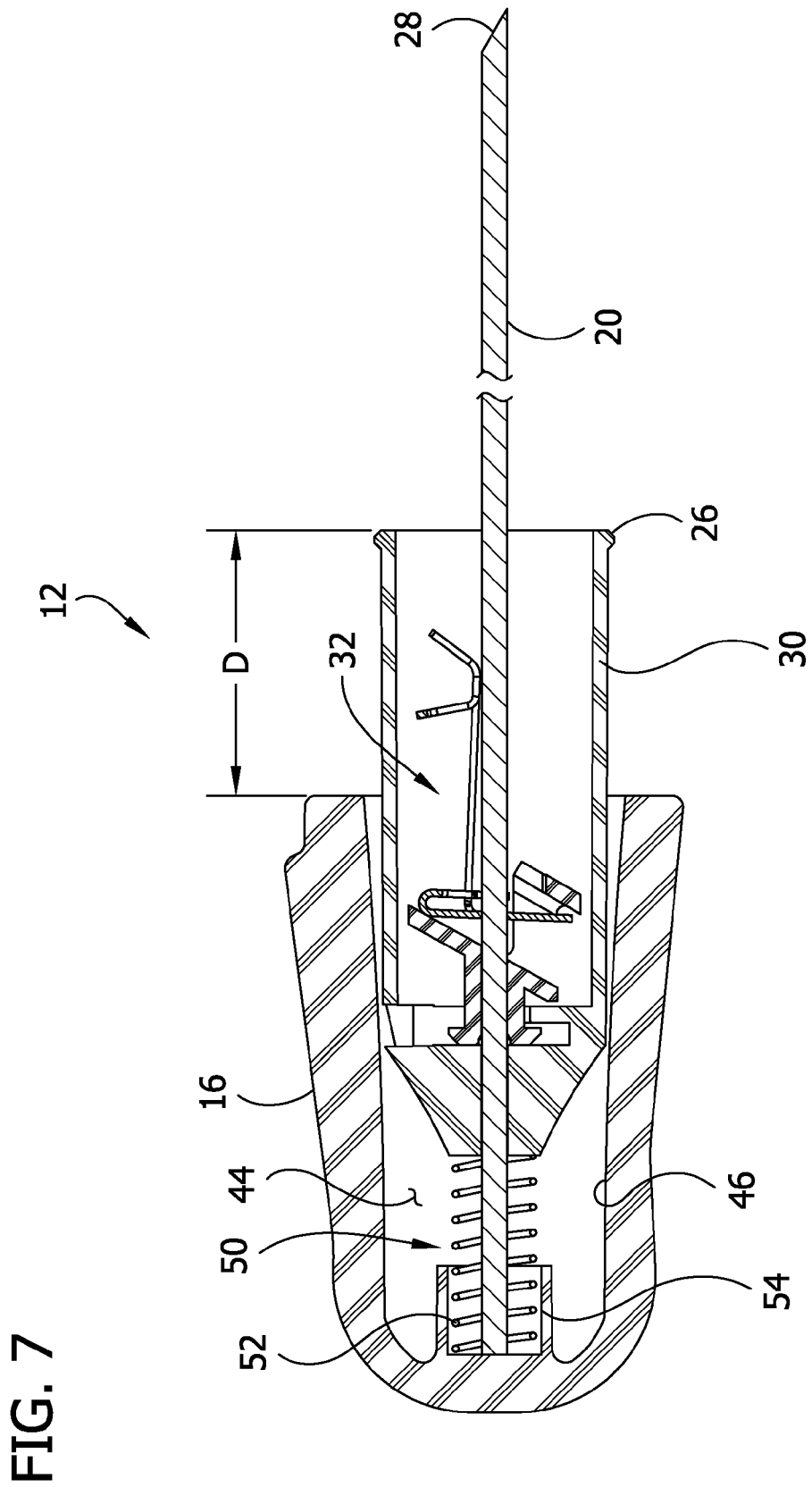
FIG. 7 is the section of FIG. 6, but showing the safety shield in an extended position.

The shield release device 50 of FIGS. 1-7 comprises a compression spring 52 received around the stylet shaft 20 within a receptacle 54 at the proximal end of the stylet handle member cavity 44. One end of the spring 52 is secured to the stylet handle member 16 and an opposite end engages a proximal end of the shield 26. When the bone needle assembly 10 is assembled and the stylet and cannula handle members 16, 18 are secured together, the distal end of the stylet shield 26 contacts the cannula handle member to move the shield into the stylet cavity 52 and compress the spring 52. FIG. 6 illustrates the stylet 12 separate from the cannula 14, but shows the retracted position of the shield 26 with the spring 52 compressed. As the stylet 12 is being axially withdrawn from the cannula 14, the compression spring 52 elongates or expands axially to urge the stylet shield 26 to move distally on the stylet shaft 20 the distance D to an extended position for allowing the user to more easily grasp the shield (FIG. 7).

Figure 8:
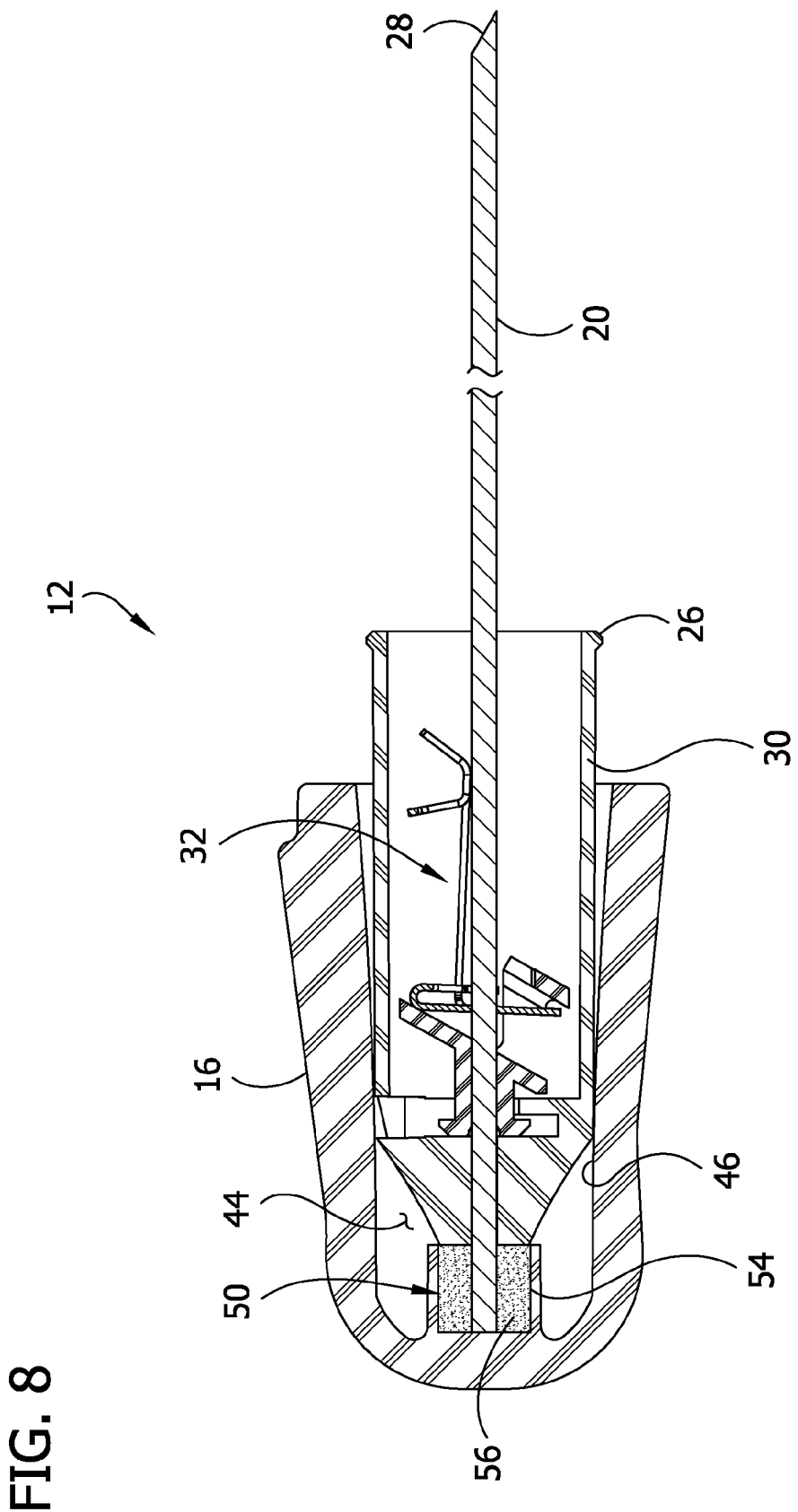
FIG. 8 is a fragmentary section of a stylet of another configuration showing a safety shield in a retracted position.
Figure 9:
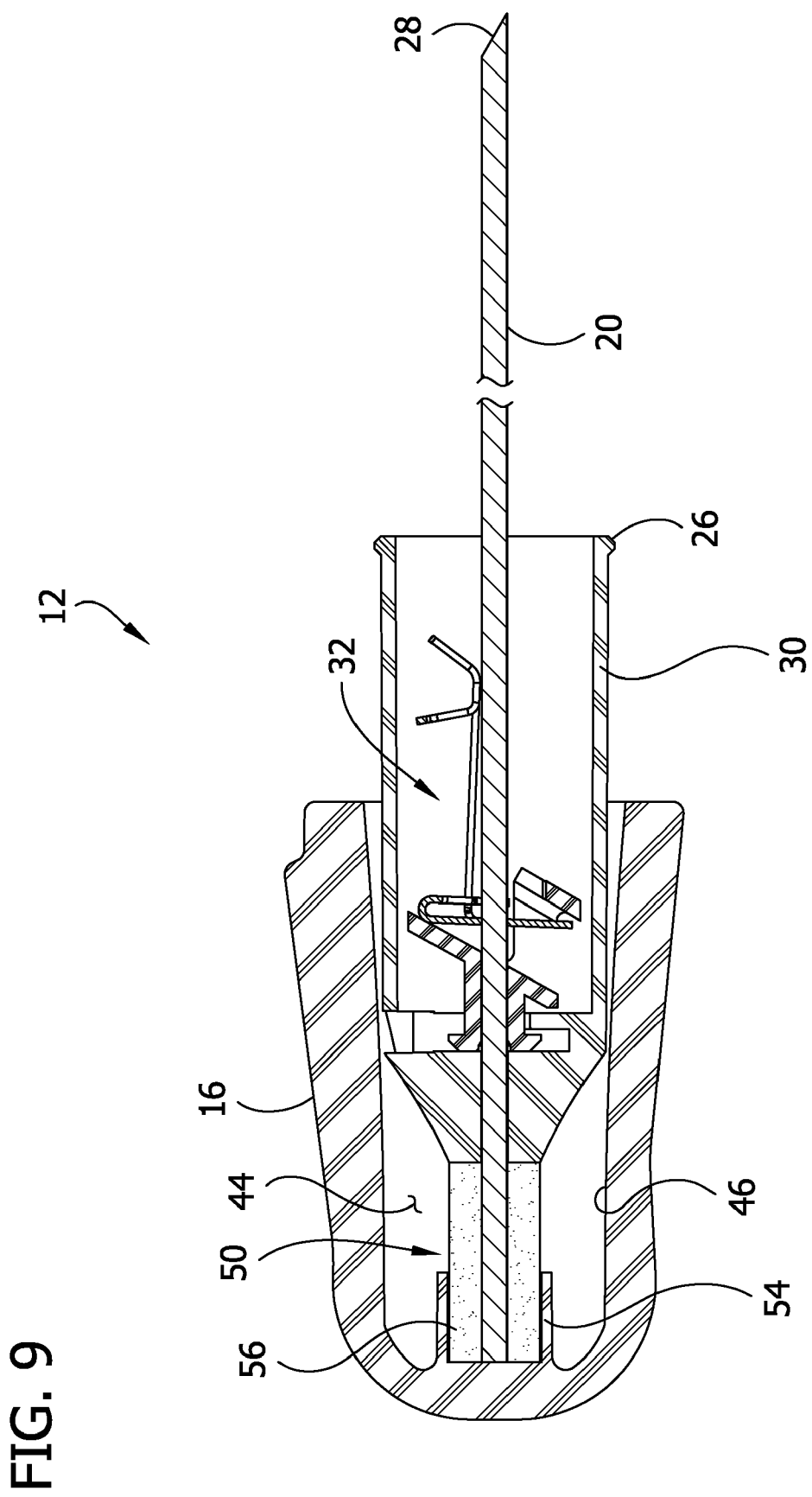
FIG. 9 is the section of FIG. 8, but showing the safety shield in an extended position.
Figure 10:
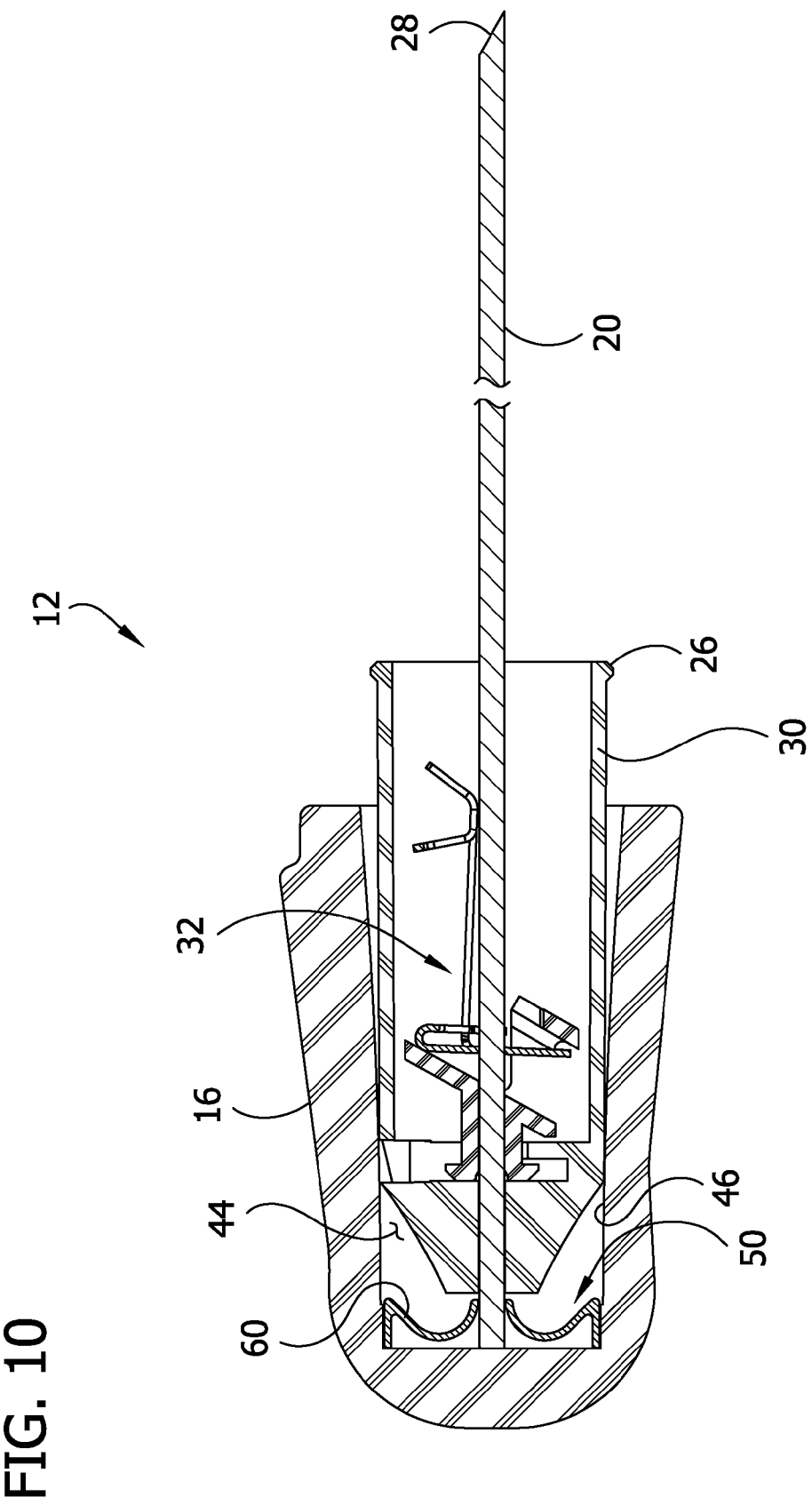
FIG. 10 is a fragmentary section of a stylet of another configuration showing a safety shield in a retracted position.
Figure 11:
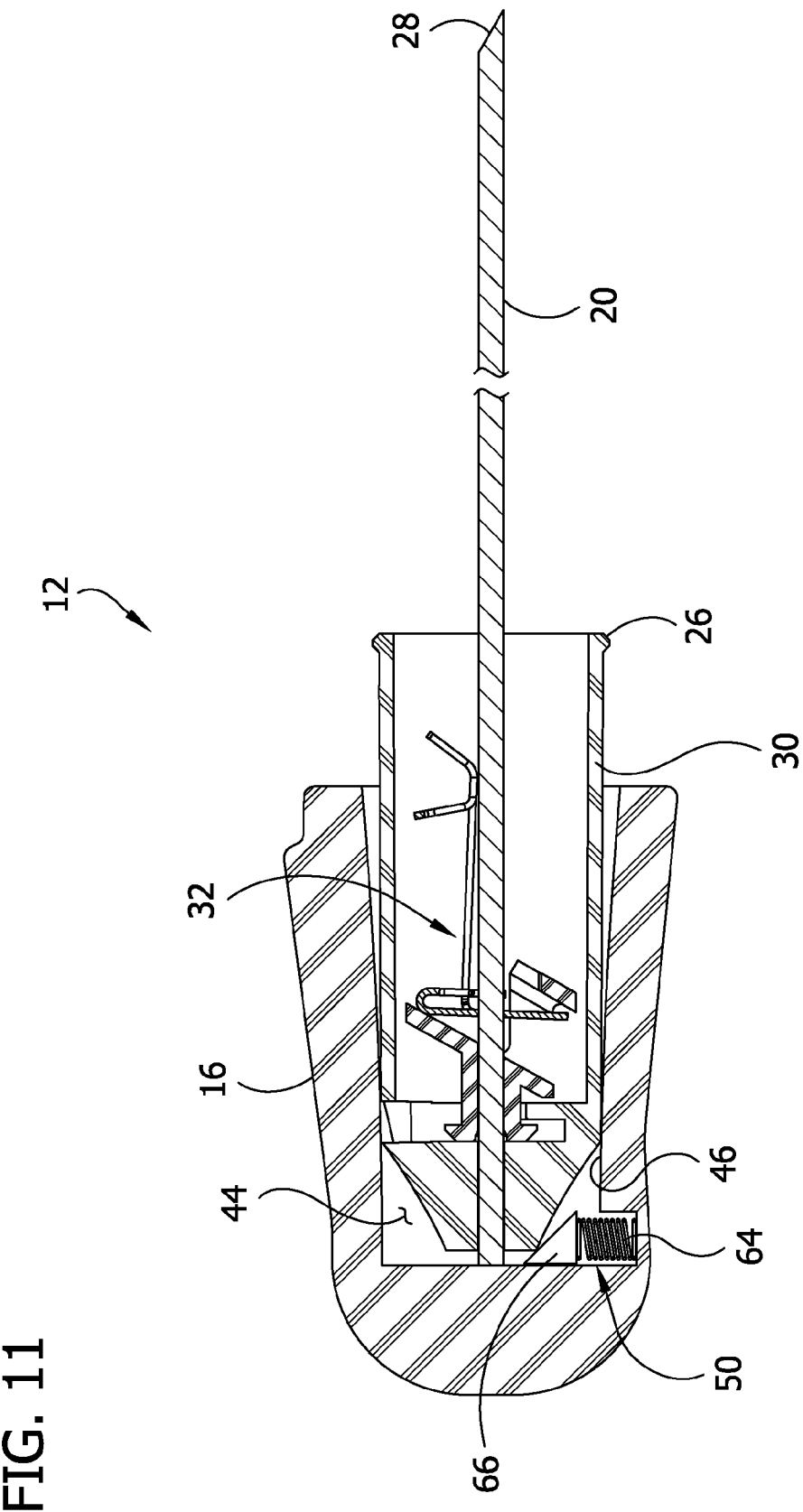
FIG. 11 is a fragmentary section of stylet of still another configuration showing a safety shield in a retracted position.

It is understood that the shield release device 50 may be of other types and configurations without departing from the scope of the present invention. For example, in the embodiment illustrated in FIGS. 8 and 9, the shield release device 50 comprises a resiliently compressible spring in the form of a tubular plug 56 received around a stylet shaft 20 within the receptacle 54 of the stylet handle member 16. In the illustrated configuration, the plug 56 is made of a foam material, but other resiliently compressible materials may be used within the scope of the present invention. Further, the shield release device 50 illustrated in FIG. 10 comprises a spring plate 60 or clip mounted in a proximal end of the stylet cavity 44. FIG. 10 shows the spring plate 60 compressed, prior to pushing the shield 26 in a direction out of the cavity 44. Yet another version of the shield release device 50 shown in FIG. 11 comprises a coil spring 64 and a wedge 66 that contacts the shield 26. In this particular embodiment, the coil spring 64 is a compression spring that exerts a force on the wedge 66 that is in a direction that is laterally transverse to the axial movement of the shield 26. The wedge 66 partially converts the laterally transverse force exerted by the spring 64 into an axially force in the direction of the movement of the shield 26. Other ways of moving a shield an axial distance from its configurations without a spring, are within the scope of the invention.

The cannula 14 also includes a safety shield 70 for covering the distal tip of the cannula shaft 22 after use. The illustrated safety shield 70 of the cannula is of the type described in U.S. patent application Ser. No. 11/146,173, filed Jun. 6, 2005, the entirety of which is herein incorporated by reference. It is understood that a cannula safety shield may be of another type or the cannula may not include a safety shield within the scope of the present invention. For purposes of the present invention, the cannula safety shield 70 will not be described in further detail herein.

In use, the bone needle assembly 10 is driven into a selected bone by grasping the handle formed by the stylet and cannula handle members 16, 18, and pushing the sharp distal ends of the stylet 12 and cannula 14 through the skin, underlying tissue and cortical bone. Description of the use of the bone needle assembly 10 is made with reference to the assembly 10 configured as shown in FIGS. 1-7. Once this penetration has been achieved, the stylet 12 is no longer required. The stylet handle member 16 is disconnected from the cannula handle member 18 by rotation through about 90° with respect to the cannula handle member. The stylet handle member 16 is then moved axially away from the cannula handle member 18 so that the stylet shaft 20 slides out of the cannula shaft 22 while the cannula shaft remains in the bone (see, FIG. 3). As the stylet 12 is withdrawn from the cannula 14, the spring 52 ("shield release device 50") moves the stylet shield 26 distally along the stylet shaft 20 the distance D from its initial position (FIG. 7). Stated another way, the stylet shield 26 is moved by the spring 52 from its FIG. 6 position to its FIG. 7 position.

After the stylet shaft 20 is completely removed from the cannula shaft 22, the technician grasps the exposed distal end portion of the stylet shield 26. Grasping the distal end of the shield 26 is facilitated by its advancement out of the stylet cavity 44 by the spring 52. The technician then slides the safety shield 26 distally along the stylet shaft 20 until the locking mechanism 32 trips and locks the shield over the sharp distal tip 28 of the shaft. The safety shield 26 is shown at an intermediate position sliding down the stylet shaft 20 in FIG. 4 and in the locked position at the end of the shaft in FIG. 5.

With the distal tip of the stylet shaft 20 safely covered by the shield 26, the cannula handle member 18 is advanced further into the bone to collect a sample of marrow, if marrow collection is the desired operation. The sharp tip 28 of the cannula 14 cuts into the bone marrow and a sample is received in the central axial passage of the cannula shaft 22. The cannula 14 can then be withdrawn from the patient by pulling on the cannula handle member 24. The sample should remain lodged in the central axial passage of the cannula shaft 22. An obturator (not shown) is then inserted into the distal tip of the cannula shaft 22 to dislodge the sample and force it out the proximal open end of the cannula shaft. The cannula safety shield 70 is then moved distally along the cannula shaft 22 until the locking mechanism in the shield (not shown) locks the shield over the tip of the shaft. It is understood that a needle assembly may be used to collect a sample other than of bone marrow within the scope of the present invention. Moreover, the cannula as located within the bone may be used for fluid injection or aspiration from the intramedulary canal.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A biopsy needle assembly comprising:

a cannula including a cannula handle and a cannula shaft extending outward from the handle, the cannula shaft having an axial passage extending through a proximal end of the shaft secured to the handle and a sharp distal tip, a stylet including a stylet handle and a stylet shaft extending outward from the stylet handle, the stylet shaft having a sharp distal tip and being adapted to be slidably received in the axial passage of the cannula shaft, the stylet handle being adapted to be releasably connected to the cannula handle when the stylet shaft is received in the cannula shaft to form a handle of the needle assembly;

a safety shield including a locking mechanism configurable between an unlocked configuration, in which the locking mechanism permits the shield to be moved axially along the stylet shaft when the shield is proximal of the tip of the stylet shaft, and a locked configuration, in which the locking mechanism prevents axial movement of the shield when the shield is at a location covering the tip of the stylet shaft, the safety shield and the handle of the stylet being adapted for releasable interengagement such that the shield moves with the stylet handle after the stylet handle and the cannula handle are released from securement with each other and as the stylet shaft is axially withdrawn from the cannula shaft; and a shield release device mounted on the stylet handle and operable for pushing the safety shield in a direction out of engagement with the stylet handle.

2. A biopsy needle assembly as set forth in claim 1 wherein the shield release device is adapted to automatically push the shield out of the stylet handle upon release of the stylet handle from the cannula handle.

3. A biopsy needle assembly as set forth in claim 2 wherein the shield release device comprises a spring.

4. A biopsy needle assembly as set forth in claim 3 wherein the spring comprises a compression spring.

5. A biopsy needle assembly as set forth in claim 4 wherein the compression spring is engageable with an inner end of the shield for biasing the shield outward from the stylet handle.

6. A biopsy needle assembly as set forth in claim 4 wherein the shield release device further comprises a wedge biased by the spring for engagement with the shield for urging the shield outward from the stylet handle.

7. A biopsy needle assembly as set forth in claim 3 wherein the spring comprises a resiliently compressible plug engageable with the shield for urging the shield outward from the stylet handle.

8. A biopsy needle assembly as set forth in claim 3 wherein the spring comprises a spring plate engageable with the shield for urging the shield outward from the stylet handle.

9. A biopsy needle assembly as set forth in claim 1 wherein the locking mechanism frictionally engages the stylet shaft when the locking mechanism is in the unlocked configuration, and wherein the frictional engagement between the locking mechanism and the stylet shaft causes the shield to move with the stylet shaft when the stylet is separated from the cannula.

10. A biopsy needle assembly as set forth in claim 1 wherein the stylet handle has a cavity formed therein for engagement with the shield to interengage the shield with the stylet handle.

11. A method of using a biopsy needle assembly comprising:

penetrating the skin with a stylet needle and cannula needle of the biopsy needle assembly;

disconnecting a stylet handle mounting the stylet needle from the cannula handle mounting the cannula needle;

separating the stylet handle and needle from the cannula handle and needle so that a stylet needle safety shield at least partially disposed in the stylet handle moves with the stylet handle;

urging the safety shield with a shield release device supported on the stylet handle from a location interior of the stylet handle outward from the interior of the stylet handle.

12. A method as set forth in claim 11 wherein the step of separating the stylet handle and needle from the cannula handle and needle includes relieving a counterforce to permit the shield release device to move the shield outward from the stylet handle.

13. A method as set forth in claim 11 wherein urging the safety shield comprises pushing the shield from a first position at least partially within the stylet handle to a second position in which more of the safety shield is exposed outside the stylet handle to facilitate grasping.

14. A method as set forth in 13 further comprising grasping the safety shield in the second position and sliding the safety shield to a location covering a sharp tip of the stylet.

15. A method as set forth in claim 14 further comprising locking the safety shield at the location covering the sharp tip.

16. A method as set forth in claim 13 wherein pushing the safety shield comprises expanding a spring operatively engaging the safety shield.

\* \* \* \* \*